US005971900A

United States Patent [19]

Miller

[11] Patent Number: 5,971,900

[45] Date of Patent: Oct. 26, 1999

[54] METHOD AND APPARATUS FOR EXERCISING AND STRENGTHENING THE HUMAN BACK

[76] Inventor: Bruce W. Miller, 4450 Gulf Blvd. #316, St. Pete Beach, Fla. 33708

[21] Appl. No.: 08/785,646

[22] Filed: Jan. 17, 1997

[51] Int. Cl.[6] .............................. A63B 21/02; A61F 5/37

[52] U.S. Cl. .............................. 482/140; 482/142; 128/876

[58] Field of Search .............................. 482/140, 142, 482/91, 124, 125, 904, 130, 126, 121, 122, 907; D21/191, 198; 128/876

[56] References Cited

U.S. PATENT DOCUMENTS

| | | | |
|---|---|---|---|
| 140,237 | 6/1873 | Austin | 482/140 |
| 837,373 | 12/1906 | Akers | 128/876 |
| 1,923,809 | 8/1933 | Bates | 128/876 |
| 4,417,726 | 11/1983 | Schleis | 482/140 |
| 4,841,961 | 6/1989 | Burlage et al. | 128/876 |
| 5,160,306 | 11/1992 | Lui | 482/904 |
| 5,372,566 | 12/1994 | Olschansky et al. | 482/140 |
| 5,551,935 | 9/1996 | Pustaver et al. | 482/142 |
| 5,626,549 | 5/1997 | Olschansky et al. | 482/140 |

*Primary Examiner*—Stephen R. Crow
*Attorney, Agent, or Firm*—Graham & James LLP

[57] ABSTRACT

An improved apparatus for exercising human back muscles and strengthening the back muscles thereby treating back muscle injuries, relieving pain caused by such injuries and increasing the strength and range of movement of the human back muscles. The apparatus includes an exercising member having a main portion, first and second leg engaging members extending from the main portion and being arranged to be wrapped around a user's legs and at least one actuating member extending from the main portion of the exercising member and being arranged to be gripped by a user's hands to allow the user to control movement of the user's legs by moving the at least one actuating member to generate mobilization to the lumbar and truncal regions of the human back.

11 Claims, 6 Drawing Sheets

METHOD AND APPARATUS FOR EXERCISING AND STRENGTHENING THE HUMAN BACK

FIELD OF THE INVENTION

The present invention relates to a method and apparatus for exercising and strengthening the muscles in the human back and more specifically, to a method and apparatus for providing variable traction and mobilization to the lumbar and truncal regions of the human back.

BACKGROUND OF THE INVENTION

Lower back pain in humans is a common and persistent ailment that is difficult to treat effectively. Lower back pain is often the result of a herniated disc, a degenerative disc disease, osteoporosis, arthritis, strained or sprained muscles and ligaments, muscle spasms or other causes.

Unfortunately, a reliable and effective treatment method for quickly and reliably curing and treating lower back pain does not exist. The most common methods of treating human lower back pain include extended periods of immobilization of the back, complete bed rest or resting of the back on a hard flat surface, bed traction and performing light exercises involving the back muscles.

Exercise is extremely beneficial for the human back, especially for treating any kind of lumbar condition, whether it is a bulging disc, herniated disc, non-surgical lumbar condition or other ailment. Simple exercises of the lumbar and spine muscle groups have a positive affect on the lumbar spine, not only for increasing range of motion but also to strengthen the area so one can endure virtually any medical condition or treatment at that area.

Conventional exercise machines provided for exercising the back and possibly treating lower back pain are typically large machines which are expensive and require a great deal of space for a person to use. In addition, the conventional machines are usually very heavy and cumbersome so that a person with an injured back may not be able to move these machines to a desired position easily and without further injuring the back muscles.

Most conventional back exercising and strengthening devices require a person to lie on their back or stomach or be seated in an upright position on a seat where the person is restrained by belts or other fastening devices. Some of these conventional machines and methods are uncomfortable for the user because of the restraints imposed on the person's body, especially if the user's back is injured. In addition, other conventional methods and machines are difficult for a user to access and mount and dismount, which creates problems especially for those persons having back injuries.

As is well known, if a muscle of the human body is strained in a manner in which it is not accustomed to, the muscle may be damaged, thereby causing pain and discomfort. The muscles of the human body associated with the lumbar and truncal regions are particularly vulnerable to such damage in part because of a natural difficulty in exercising these muscles of the body in an effective manner. It seems most natural to exercise these muscles through bending or stretching exercises while in a standing or sitting position. Yet when a person's back is in a generally vertical orientation relative to the ground or surface upon which the person is standing, gravity introduces an axial loading on the spinal joints that inhibits the full motion of the paraspinous muscles, thereby limiting the effectiveness of exercising these muscles while in a vertical orientation. Proper exercising of the back muscles can be accomplished most readily only when a person is in a substantially horizontal orientation relative to the ground or a supporting surface.

Given the natural difficulty in exercising the lower spinal muscles, several devices have been designed to facilitate exercising of this area. These devices usually require a person to stand or sit in an essentially vertical position during use and exercising, thereby forcing the user to overcome axial loading caused by gravity in order to fully extend and exercise their paraspinous muscles. This orientation during exercise increases the difficulty of the exercises and reduces the efficacy of the exercises and results achieved.

SUMMARY OF THE PRESENT INVENTION

The preferred embodiments of the present invention overcome the disadvantages of the conventional methods and machines for exercising and treating human back muscles by providing an improved method and apparatus for exercising and strengthening the back muscles thereby treating back muscle injuries, relieving pain caused by such injuries and increasing the strength and range of movement of the human back muscles.

The preferred embodiments of the present invention also provide a method and apparatus for easily and economically exercising and strengthening the human back muscles, wherein the improved apparatus is inexpensive, portable, easily stored and transported, and yet highly effective for treating back injuries, relieving back pain, strengthening back muscles and improving range of motion of the back muscles.

According to one preferred embodiment of the present invention, an improved apparatus for exercising human back muscles includes an exercising member having a main portion, first and second leg engaging members extending from the main portion and being arranged to be wrapped around a user's legs and at least one actuating member extending from the main portion of the exercising member and being arranged to be gripped by a user's hands to allow the user to control movement of the user's legs by moving the at least one actuating member.

The exercising member may comprise a single unitary member fabricated entirely from a single unitary material. Alternatively, the exercising member may comprise a single member fabricated of two or more interconnected portions. For example, the main portion and the first and second leg engaging members extending from the main portion may be preferably formed from a first single, unitary material member while the at least one actuating member may be formed from a second single unitary material member which is connected to the first single, unitary material member.

In the preferred embodiment described above, the exercising member preferably comprises a fabric or cloth material or other suitable flexible material which can be rolled or folded into a compact unit when not in use so as to minimize space requirements and to render it highly portable. The main portion-preferably comprises a substantially square or rectangular member which is adapted to fit over the feet of a user.

Furthermore, the first and second leg engaging members preferably comprise elongated strips which extend from opposite sides of the main portion in opposite directions. Each of the first and second leg engaging members is preferably located adjacent to a side of the main portion from which the opposite portions of the at least one actuating member extend. The leg engaging members and the main portion are preferably made from the same material and the at least on actuating member may be made from the same or different material used for the main portion and the leg engaging members. Each of the leg engaging members preferably include a connecting or fastening member, such as a VELCRO fastening member or other suitable structure, for being removably connected to the other of the leg engaging members.

As will be explained in more detail below, the leg engaging members are arranged to be wrapped around the feet and/or legs and support the legs during exercise without causing any force whatsoever on the spinal muscles and lumbar spine. Without the stress or gravity imparting a force on the back muscles and spinal muscles, the back muscles are free to be completely and safely exercised.

The at least one actuating member preferably comprises an elongated strap and is preferably connected to the main member such that first and second ends of the at least one actuating member are spaced from each other and substantially parallel to each other. The at least one actuating member may comprise the same or different material as the main portion and the leg engaging members and may be connected via a suitable known connection to the main portion. The at least one actuating member is used to facilitate a desired range of motion of a user's legs above the ground or support surface upon which the user is supported. The range of motion of the legs, to be described in more detail below, will cause rotation of the lumbar spine and lateral flexion of the lumbar spine.

The preferred embodiments of the present invention also provide an improved method of exercising human back muscles, the method including the steps of providing an exercising member having a main portion, first and second leg engaging members extending from the main portion and being arranged to be wrapped around a user's legs and the at least one actuating member extending from the main portion of the exercising member and being arranged to be gripped by a user's hands; placing the main portion on a user's feet; wrapping the first and second leg engaging members around at least one of the leg portion and the feet of a user; wrapping ends of the first and second leg engaging members around an upper leg portion of each of the user's legs; connecting the first and second leg engaging members to each other; gripping the at least one actuating member; and using the at least one actuating member to impart motion to the legs of a user.

According to the preferred method described above, the user is lying in a supine position and once the exercising member is positioned on the user's body as described above, the user's legs are arranged in a substantially L-shaped orientation. By pulling on the first and second ends of the at least one actuating member, the legs can be moved in a rotary or in a lateral reciprocal motion to generate lumbar mobilization while eliminating all effects of gravity and other stress on the lower back to enable exercise having increased effectiveness and range of motion.

Such lumbar mobilization increases the range of motion in the lumbar spine so that when the exercise according to the preferred method of the present invention is done, the invention strengthens the ligamentous tissue around the L4/L5, L5/S1 and sacroiliac joint and increases mobilization of the muscles which may prevent injury to those muscles in the future.

The concept of lumbar mobilization involves movement of the lumbar spine. Common mobilization of the lumbar spine may include flexion, extension, left and right lateral flexion, and left and right rotation. The type of motion that is created with the apparatus and method of the preferred embodiments of the present invention involves the sacral joint as well as L5 and S1. This movement would commonly be known as lateral flexion of the spine. However with the apparatus and method of the preferred embodiments of the present invention, instead of generating such movement from the upper spine down through the lower area which would not affect the thoracic spine as is conventionally done, the preferred embodiments of the present invention provide a range of motion which affects the sacroiliac joint, L5/S1 and L4/L5 in a motion that is not achieved through conventional lumbar exercise programs and equipment.

These and other features and advantages of the preferred embodiments of the present invention will become apparent from the detailed description of the preferred embodiments of the present invention as illustrated in the following drawings.

DETAILED DESCRIPTION OF PREFERRED EMBODIMENTS

Figure 1:
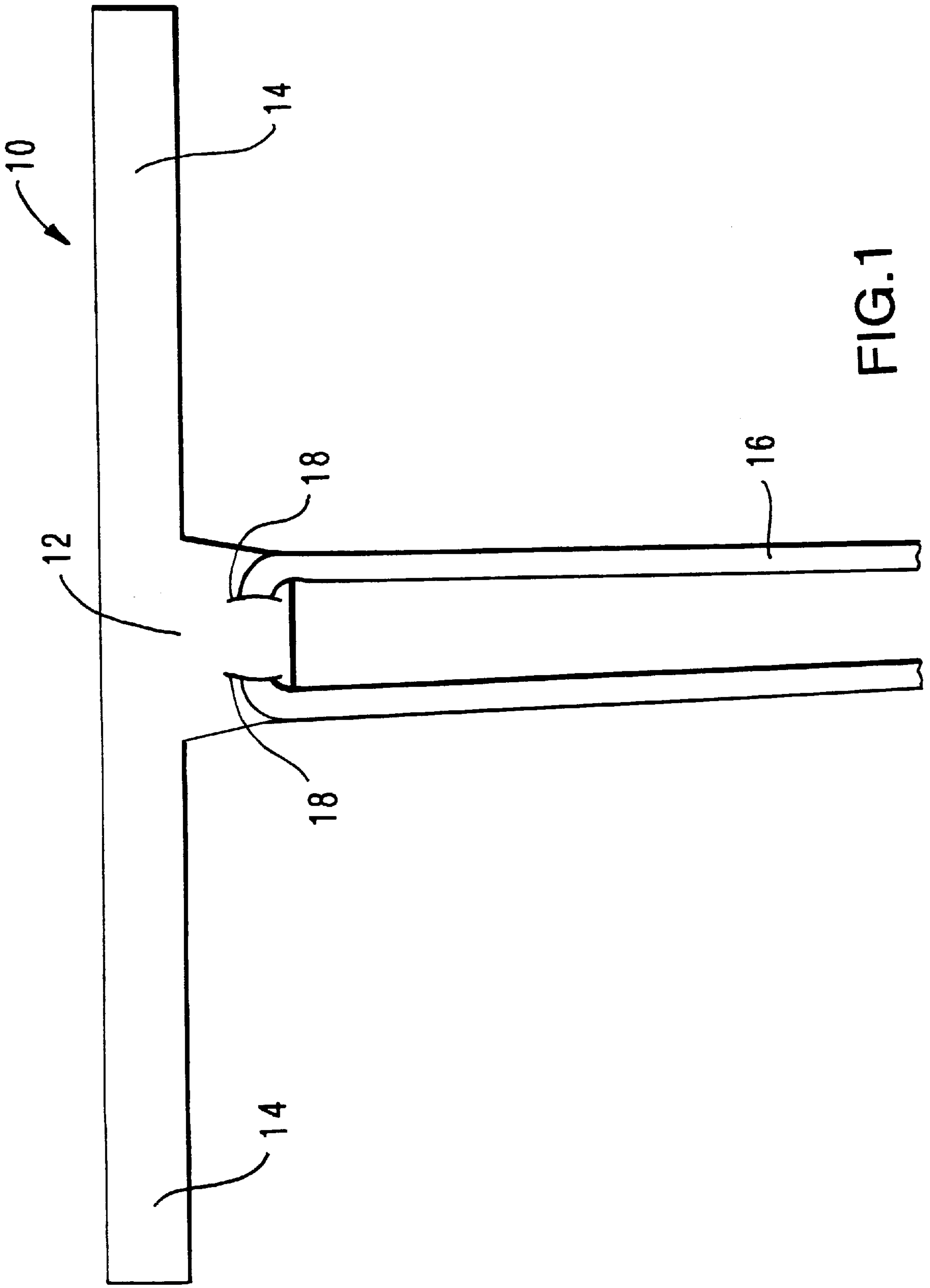
FIG. 1 is a view of an improved apparatus for exercising and strengthening human back muscles.

Referring now to the figures where like reference numerals indicate like elements, FIG. 1 shows a preferred embodiment of the apparatus 10 for exercising and strengthening the muscles of the human back. The apparatus 10 preferably includes a main portion 12 disposed at a substantially central location of the apparatus 10. First and second leg engaging members 14 preferably in the form of elongated members are preferably attached to the main portion 12 and extend in opposite directions from the main portion 12. In addition, at least one actuating member 16 preferably in the form of straps is attached to the main portion 12. As seen in FIG. 1, the actuating member 16 can be movably inserted in two slits 18 formed in the main portion 12 so as to allow the actuating member 16 to be adjusted relative to the main portion 12 and the leg engaging members. Alternatively, two or more actuating members 16 may be connected to the main portion via stitching, fasteners or other suitable connecting members.

The apparatus 10 shown in FIG. 1 preferably comprises an exercising member 10 wherein the main portion 12 is arranged to be located on a user's feet, the first and second leg engaging members 14 are arranged to be wrapped around a user's legs and the at least one actuating member 16 extending from the main portion 12 is arranged to be gripped by a user's hands to allow the user to control movement of the user's legs by moving the at least one actuating member 16 as will be described in the following paragraphs.

A preferred embodiment of the apparatus 10 is preferably made of a fabric or cloth material or other suitable flexible material which can be rolled or folded into a compact unit when not in use so as to minimize space requirements and to render it highly portable.

The main portion 12 preferably comprises a substantially square or rectangular member which is adapted to fit over the feet of a user.

Furthermore, the first and second leg engaging members 14 preferably comprise elongated strips which extend from opposite sides of the main portion 12 in opposite directions. Each of the first and second leg engaging members 14 is preferably located adjacent to a side of the main portion 12 from which the first and second ends of the at least one actuating member 16 extend. Each of the leg engaging members 14 preferably include a connecting or fastening member, such as a VELCRO fastening member or other suitable structure, for being removably connected to the other of the leg engaging members 14.

In one preferred embodiment, the apparatus 10 can be made of a single, unitary member formed entirely of the same material, such as, a fabric or cloth material or other suitable flexible material. In another preferred embodiment, the main portion 12 and the leg engaging members 14 may be formed of a first material and the at least one actuating member 16 may be formed of a second material which is different from the first material used to form the main portion 12 and the leg engaging members 14. Furthermore, the main portion 12, the leg engaging members 14 and the at least one actuating member may all be formed from three different materials as desired.

Figure 2:
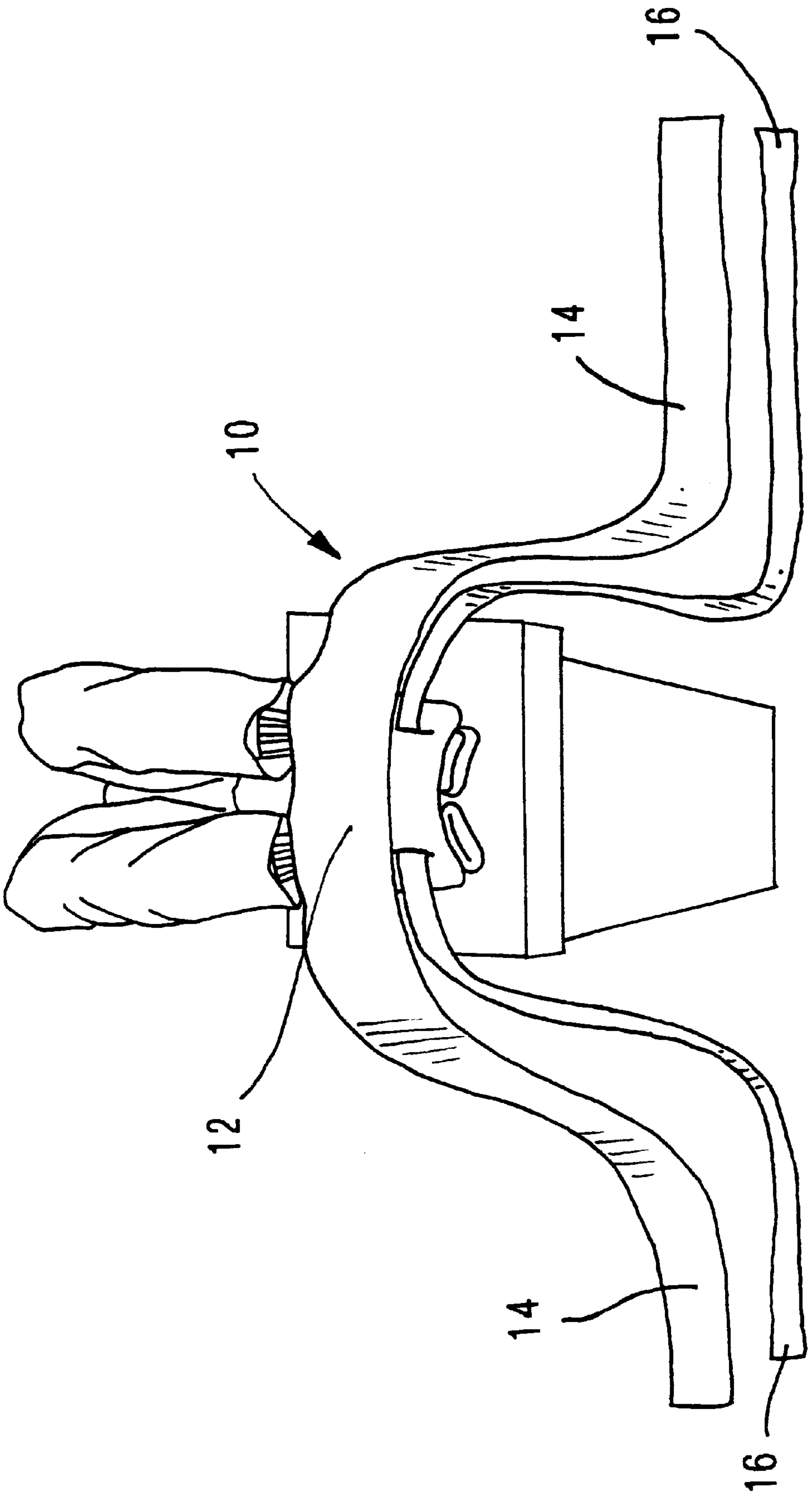
FIG. 2 is a view of an initial installation position of the apparatus shown in FIG. 1 on a user.

FIG. 2 shows an initial mounting position of the apparatus 10 on a user. As seen in FIG. 2, the main portion 12 is located on the feet of a user. The leg engaging members 14 are disposed to extend on either side of the feet. The at least one actuating member 16 is also disposed to extend to both sides of the feet. As will be explained in more detail below, the leg engaging members 14 are arranged to be wrapped around the feet and/or legs and support the legs during exercise without causing any force whatsoever on the spinal muscles and lumbar spine. Without the stress or gravity imparting a force on the back muscles and spinal muscles, the back muscles are free to be completely and safely exercised.

Figure 3:
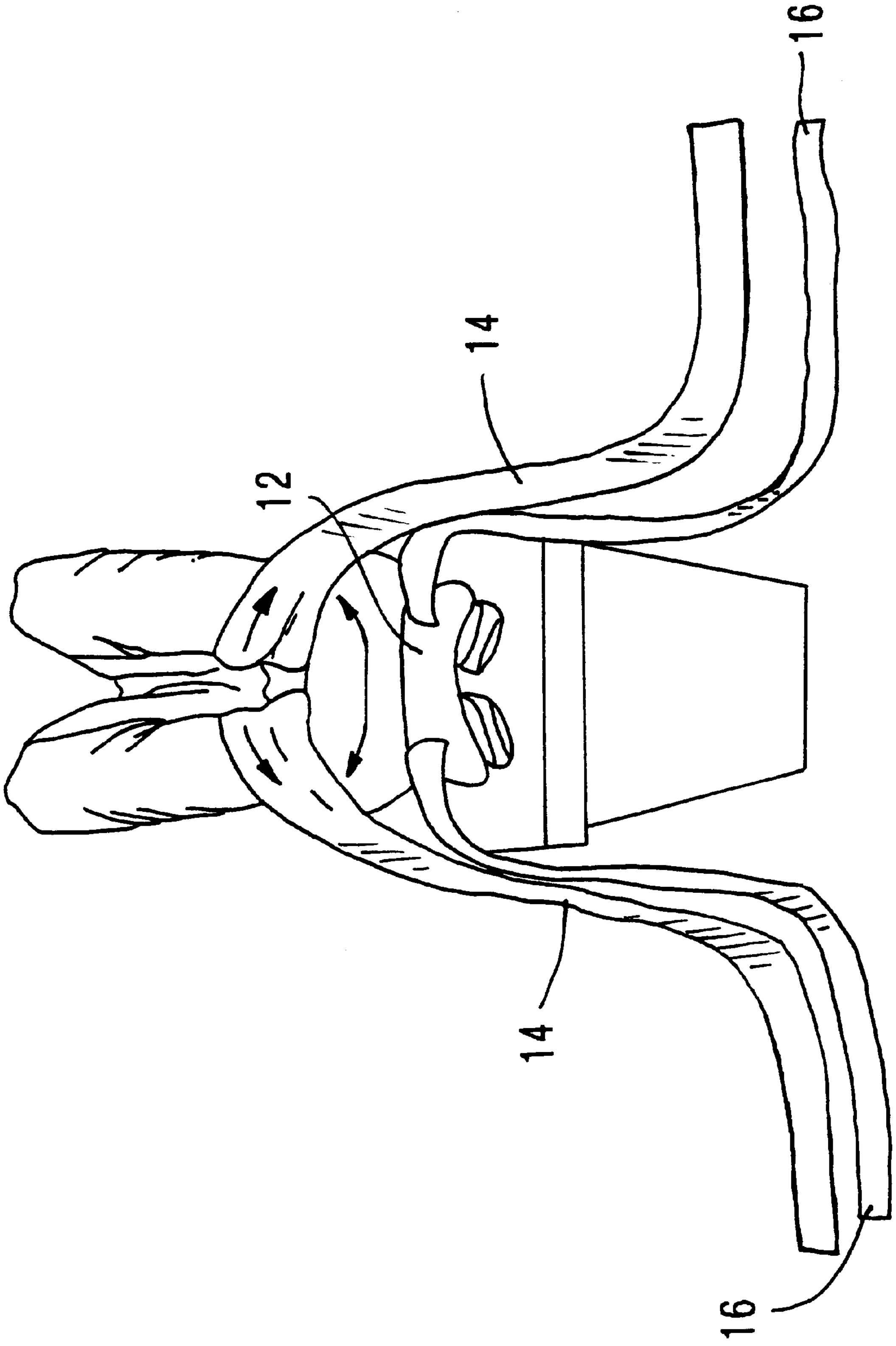
FIG. 3 is a view illustrating a wrapping process for wrapping the apparatus shown in FIG. 1 onto a user.

As seen in FIG. 3, the leg engaging members 14 are wrapped around the legs of the user by bringing the members 14 over the lower extremity and over the leg with the right side portion extending back to the right and the left side portion extending to the left. In a preferred method, the members 14 are wrapped around the ankle area as seen in FIG. 3.

Figure 4:
FIG. 4 is a view illustrating a final wrapped arrangement of the apparatus shown in FIG. 1.

FIG. 4 shows the leg engaging members 14 being completely wrapped twice around the ankles and then around the legs. As seen in FIG. 4, the legs are held in a substantially L-shaped arrangement so as to remove any stress or force of gravity on the back.

Figure 5:
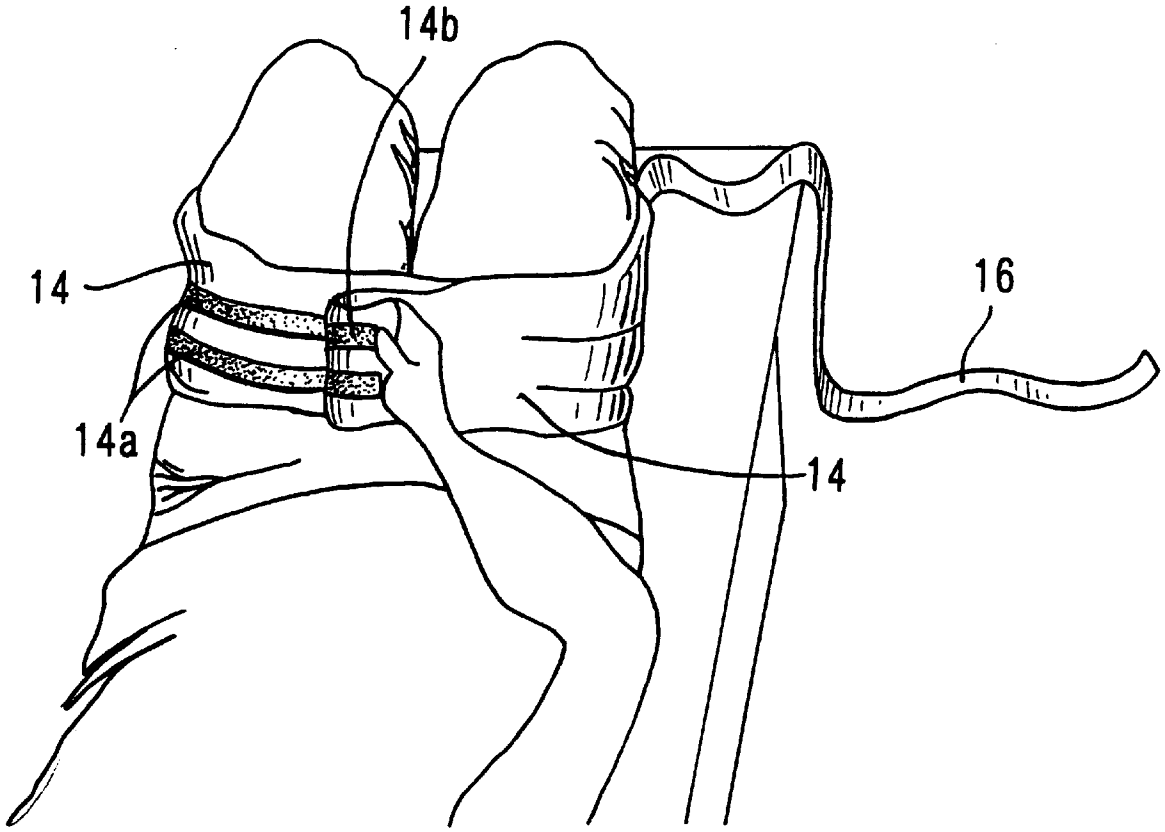
FIG. 5 is a view of first and second engaging members being attached to each other so as to secure the apparatus shown in FIG. 1 to the user.

FIG. 5 shows a locking or connecting mechanism for attaching opposite ends of the leg engaging members 14 so as to tightly wrap the legs of the user into the substantially L-shaped position. The locking or connecting mechanism preferably includes cooperating attaching members 14*a* and 14*b* disposed on opposite ends of the leg engaging members 14. The attaching members 14*a*, 14*b* preferably comprise a VELCRO fastening member engaging members but may also comprise any known connecting mechanism. As seen in FIG. 5, once the attaching members 14*a*, 14*b* are connected to each other, the leg engaging members 14 are engaged and hold the upper and lower portions of the user's legs in a substantially L-shaped arrangement.

Figure 6:
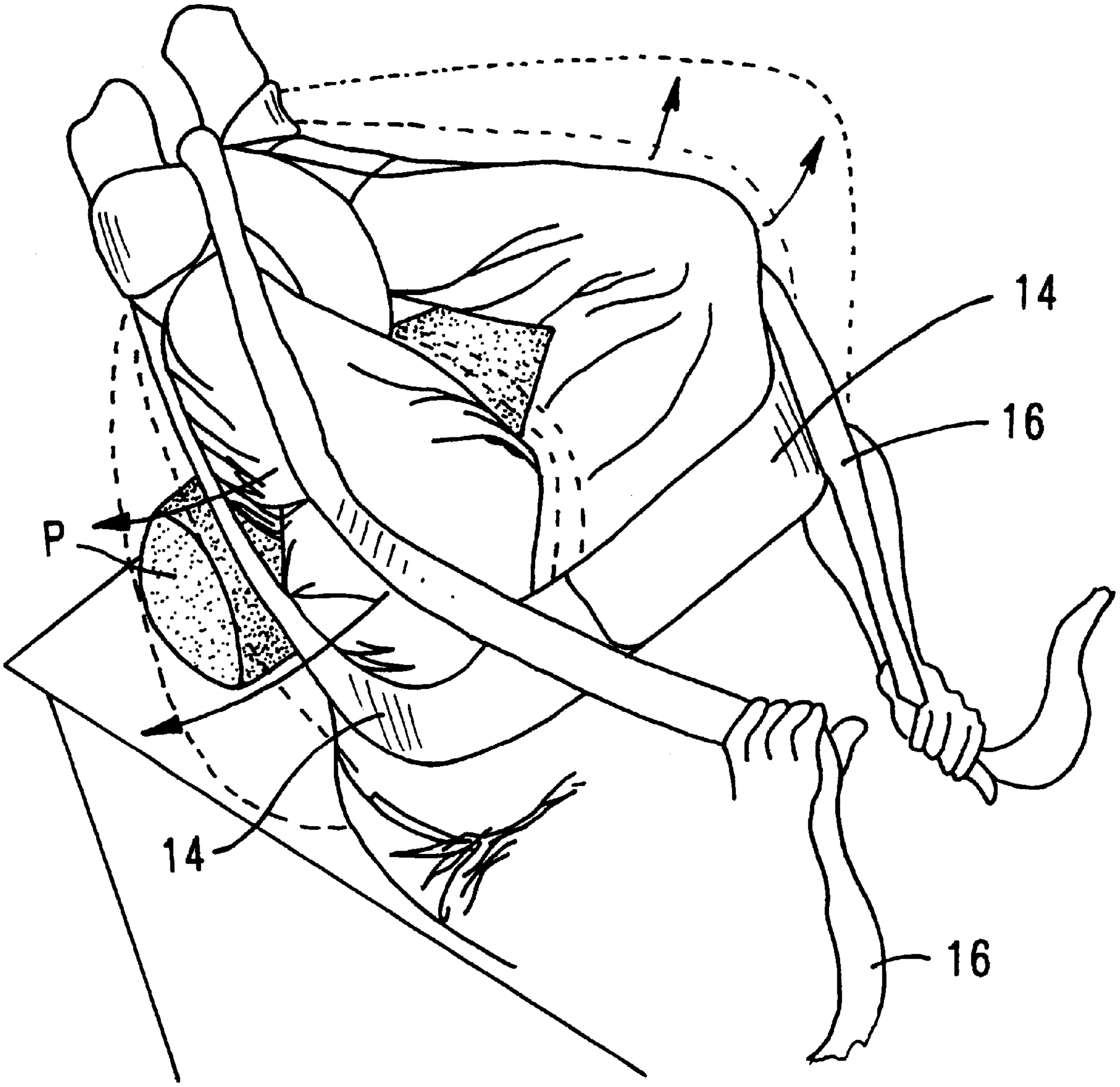
FIG. 6 is a view of the apparatus shown in FIG. 1 being used with an optional pillow disposed in a L-shaped area defined by a user's legs.

In an alternative embodiment, a different way of wrapping the lower ankle portion involves making one wrap around the ankle and another wrap around the feet then looping the leg engaging members 14 over the thighs in a locking position similar to what is shown in FIGS. 4–6.

In each of the arrangements shown in FIGS. 4–6, the user is lying down and the legs are held by the apparatus in a substantially L-shaped arrangement. The apparatus 10 is preferably arranged to be wrapped around the ankles or lower leg portion of a user once or twice and possibly around the feet and then wrapped around the upper thigh area of the user. Then, the apparatus 10 is locked into position on a user by attaching the attaching members 14*a*, 14*b* disposed on opposite ends of the leg engaging members 14 to each other.

Then, as seen in FIG. 6, the at least one actuating member 16 is pulled and moved by the user to propel the lumbar spine in a left and right lateral flexion. As a result of the structure and arrangement of the apparatus 10 on the user, all of the weight bearing factors are off the lumbar spine at the sacroiliac joint, L4/L5 articulation and L5/S1 articulation. All the gravity and weight bearing factors are removed and therefore, increased mobility is achieved in this position shown in FIGS. 4–6.

More specifically, FIG. 6 shows in phantom and dark lines, the reciprocal lateral movement or swishing motion that is generated by gripping and moving the actuating member 16 so as to exercise the lower back of the user. The actuating member 16 is gripped at the two ends thereof and is used to swish left and right with the forces of gravity being held off of the L4/L5, L5/S1 and sacroiliac articulations by the apparatus 10 so that increased mobilization of the lower back area can be accomplished.

As seen in FIG. 6, the legs of a user are arranged in an L-shaped position and a pillow P can be inserted underneath the L-shaped portion of the legs of the user such that the upper and lower portions of the legs can rest on the pillow P so as to take some of the weight off the lower portion of the lower leg extremity. The pillow P can make the motion and the apparatus more comfortable.

While the invention has been particularly shown and described with reference to the preferred embodiments of the present invention, it will be understood by those skilled in the art that the foregoing and other changes in form may be made therein without departing from the spirit and scope of the invention.

What is claimed is:

1. An apparatus for exercising human back muscles comprising:

a main portion, adapted to be located on a user's feet; first and second leg engaging members extending from the main portion and being adapted to be wrapped around a user's legs;

said first and second leg engaging members being adapted to be wrapped around said legs above and below the knees of the user; and at least one actuating member extending from the main portion adapted to be gripped by a user's hands to allow the user to control movement of the user's legs by moving at least one actuating member so as to impart lumbar mobilization.

2. The apparatus according to claim 1, wherein the main portion, the first and second leg engaging members and the at least one actuating member comprise a single unitary exercising member made from a single material.

3. The apparatus according to claim 1, wherein the main portion, the first and second leg engaging members and the main portion are made of a first material and the at least one actuating member is made from a second material that is different from said first material.

4. The apparatus according to claim 1, wherein the main portion comprises a substantially square or rectangular member which is adapted to fit over the feet of a user.

5. The apparatus according to claim 1, wherein the first and second leg engaging members comprise elongated strips which extend from opposite sides of the main portion in opposite directions.

6. The apparatus according to claim 1, wherein each of the first and second leg engaging members is located adjacent to a side of the main portion from which the at least one actuating member extend.

7. The apparatus according to claim 1, wherein each of the leg engaging members includes a fastening member for being removably connected to the other of the leg engaging members.

8. The apparatus according to claim 1, wherein the leg engaging members are arranged to be wrapped around at least one of the feet, the ankles and the legs of a user and to support the legs during exercise minimizing any forces on the spinal muscles and lumbar spine of the user.

9. The apparatus according to claim 1, wherein the at least one actuating member comprises elongated straps and are connected to the main portion such that the first and second leg engaging members are capable of being spaced from each other and substantially parallel to each other.

10. The apparatus according to claim 1, wherein the at least one actuating member is used to impart motion to a user's legs above a support surface upon which the user is supported so as to generate lumbar mobilization in the user.

11. The apparatus according to claim 1, wherein the at least one actuating member is arranged to impart rotation and lateral flexion of the lumbar spine of the user.

* * * * *